United States Patent [19]

Steigerwald

[11] Patent Number: 4,521,213

[45] Date of Patent: Jun. 4, 1985

[54] LIQUID DRAINAGE SYSTEM WITH HINGED CUP-SHAPED VALVE

[75] Inventor: Carl J. Steigerwald, Wauconda, Ill.

[73] Assignee: The Kendall Company, Boston, Mass.

[21] Appl. No.: 465,375

[22] Filed: Feb. 10, 1983

[51] Int. Cl.³ .............................................. A61M 1/00
[52] U.S. Cl. .................................. 604/323; 604/335; 604/350
[58] Field of Search .................. 604/317, 322–326, 604/335, 350; 128/760, 762, 766, 767; 137/855–858, 527.6

[56] References Cited

U.S. PATENT DOCUMENTS

| 2,001,885 | 5/1935 | Ohmart | 137/855 |
| 2,954,640 | 10/1960 | Catalano et al. | 137/855 |
| 3,066,696 | 12/1962 | Hansley | 137/855 |
| 3,529,599 | 9/1970 | Folkman | 604/323 |
| 3,586,041 | 6/1971 | Monestere | 604/323 |
| 4,305,404 | 12/1981 | Dunn | 128/767 |

Primary Examiner—Stephen C. Pellegrino
Assistant Examiner—J. L. Kruter
Attorney, Agent, or Firm—Powell L. Sprunger

[57] ABSTRACT

A liquid drainage system comprising, a receptacle having a chamber to receive liquid, and a depending annular wall in an upper portion of the receptacle. The system has a valve comprising a cup-shaped member of elastic material having a lower wall extending across the cup-shaped member, an upper annular wall extending from the lower wall, with an upper portion of the valve annular wall being snugly received on a lower portion of the receptacle wall, and a hinge member extending outwardly from the cup-shaped member at one side of the lower wall. The cup-shaped member has a slit extending through the cup-shaped member to the hinge member at a location slightly above the lower wall. The slit defines a valve seat above the lower wall with the lower wall serving as a valve element which may sealingly engage against the seat, with the hinge member connecting the lower wall and valve annular wall.

7 Claims, 4 Drawing Figures

U.S. Patent    Jun. 4, 1985    4,521,213
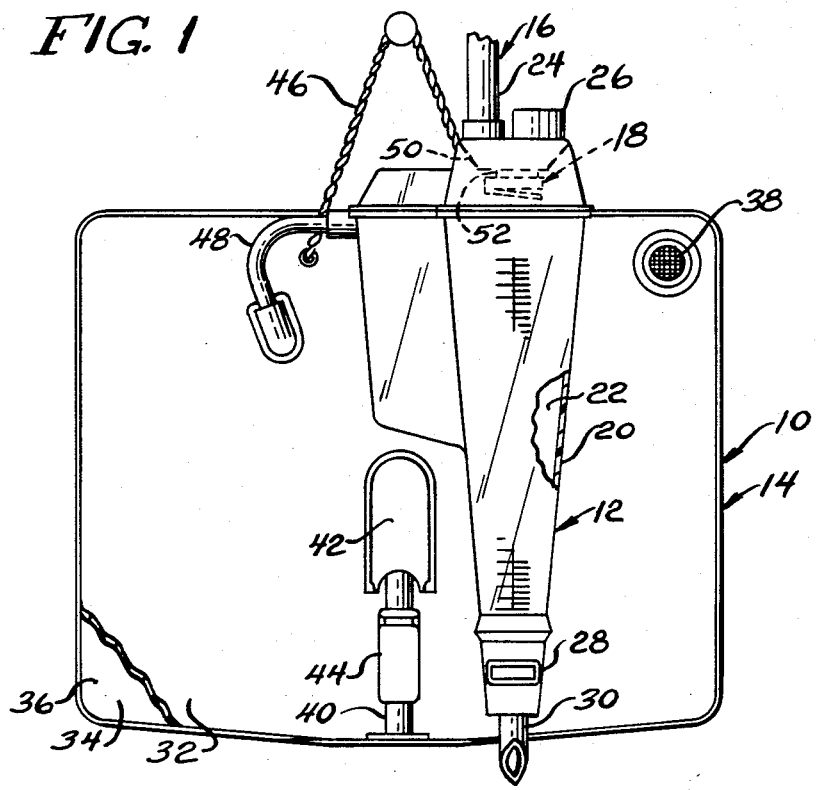
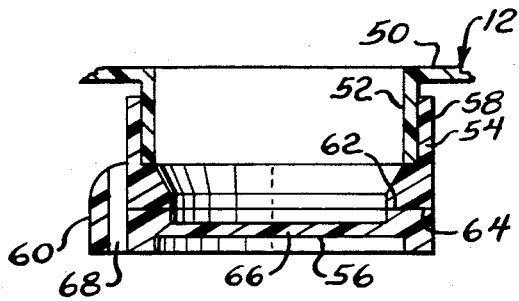
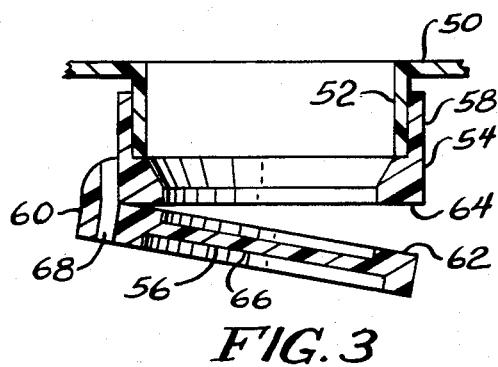

4,521,213

LIQUID DRAINAGE SYSTEM WITH HINGED CUP-SHAPED VALVE

BACKGROUND OF THE INVENTION

The present invention relates to liquid drainage systems, and more particularly to urine drainage systems.

Urine drainage systems, such as urine meters, have been proposed in the past. Such systems may comprise a receptacle having a chamber, a container having a cavity, a catheter, and a drainage tube communicating between the catheter and receptacle. The catheter is passed through the urethra of a patient until a drainage eye in a distal portion of the catheter is located in the patient's bladder. During use, urine drains from the bladder through the drainage eye, the catheter, and drainage tube into the receptacle where the urine output is collected and measured.

In one form, the system may have a conduit communicating between an upper portion of the chamber and an upper portion of the cavity. When it is desirable to empty urine from the receptacle, such as when it is full, the receptacle is tilted, and the urine passes from the chamber through the conduit into the cavity for retention therein. Normally, the receptacle would be provided with a vent in an upper portion of the receptacle having a bacteria filter in order to facilitate the emptying procedure from the receptacle into the container. However, it is desirable to prevent contact of the filter by the urine when the receptacle is being emptied, since such contact may render the filter inoperable. Also, it is desirable to prevent the reflux of urine into the drainage tube, since such refluxing urine may contain bacteria which may by retrograde movement pass from the drainage tube into the bladder with possible deleterious results to the patient.

SUMMARY OF THE INVENTION

A principal feature of the present invention is the provision of an improved liquid drainage system of simplified construction.

The liquid drainage system of the present invention comprises, a receptacle having a chamber to receive liquid, and a depending annular wall in an upper portion of the receptacle. The system has a valve comprising a cup-shaped member of elastic material having a lower wall extending across the cup-shaped member, an upper annular wall extending from the lower wall, with an upper portion of the valve annular wall being snugly received on a lower portion of the receptacle wall, and a hinge member extending outwardly from the cup-shaped member at one side of the lower wall. The cup-shaped member has a slit extending through the cup-shaped member to the hinge member at a location slightly above the lower wall.

A feature of the present invention is that the slit defines a valve seat above the lower wall with the lower wall serving as a valve element which may sealingly engage against the seat, while the hinge member connects the lower wall and valve annular wall.

Another feature of the present invention is that the valve element is in an open position spaced from the seat when the receptacle is placed in an upright position.

Thus, a feature of the present invention is that the valve element automatically permits passage of urine past the seat when the receptacle is placed in an upright position.

Still another feature of the invention is that the valve element automatically closes against the seat when the receptacle is placed in an inverted position.

Yet another feature of the invention is that the valve element closes when refluxing urine in the receptacle chamber strikes the valve element.

Thus, a feature of the present invention is that the valve element is closed against the seat when the receptacle is tilted in order to pour liquid from the receptacle chamber.

Further features will become more fully apparent in the following description of the embodiments of this invention and from the appended claims.

DESCRIPTION OF THE DRAWINGS

In the drawings:

FIG. 1 is a fragmentary elevational view of a liquid drainage system of the present invention;

FIG. 2 is a fragmentary sectional view illustrating a valve of the system in a closed position;

FIG. 3 is a fragmentary sectional view illustrating the valve in a closed position against a seat; and FIG. 4 is an upper plan view of the valve. DESCRIPTION OF THE PREFERRED EMBODIMENTS Referring now to FIG. 1, there is shown a liquid drainage system generally designated 10 comprising a receptacle 12, a container 14, a drainage tube 16, and a valve 18 in the receptacle 12. The receptacle 12 has a rigid outer wall 20, such as a suitable plastic material, defining a chamber 22 in the receptacle 12. As shown, a downstream end 24 of the drainage tube 16 communicates with an upper portion of the chamber 22 at a location above the valve 18. The receptacle 12 may have a vent 26 containing a bacteria filter of known type which communicates between the chamber 22 and the atmosphere in order to remove bacteria from the air passing through the vent 26 into the chamber 22. In a preferred form, as shown, the vent 26 is located above the valve 18. The receptacle 12 may also have a valve 28 of known type in order to empty urine from the chamber 22 through a tubular section 30, if it is desired to obtain a sample of the urine.

The container 14 has a front wall 32 of flexible plastic material, and a back wall 34 of flexible plastic material, with the front and back walls 32 and 34 being joined at their periphery in order to define a cavity 36 between the front and back walls 32 and 34. The container 14 may have a vent 38 having a bacteria filter of known type communicating between the cavity 36 and the atmosphere in order to remove bacteria from the air passing from the atmosphere into the cavity 36. The container 14 may have a lower tubular section 40 with an outer end received in a pocket 42 on the front wall 32 in a storage position of the tubular section 40. When it is desired to drain urine from the cavity 36, the tubular section 40 is removed from the pocket 42, and a clamp 44 of known type on the tubular section 40 is opened to permit passage of urine through the tubular section 40. After drainage of urine from the cavity 36, the clamp 44 is again closed, and the tubular section 40 is placed in the pocket 42 in the storage position of the tubular section 40. The container 14 may have a cord 46 secured to an upper portion of the container 14 in order to hang the receptacle 12 and container 14 from a suitable object, such as a bed rail, with an upper portion of the receptacle 12 being releasably retained on an upper portion of the container 14. As shown, the system 10 may have a flexible conduit 48 which communicates between an upper portion of the chamber 22 and an upper portion of the cavity 36 for a purpose which will be described below.

In use of the system 10, a catheter (not shown) is passed through the urethra of a patient until a drainage eye in a distal end of the catheter is located in the patient's bladder. In this configuration, a proximal end of the catheter located outside the patient's body is connected to an upstream portion of the drainage tube 16. Urine drains through the drainage eye, the catheter, and the drainage tube 16 into the receptacle 12 where the urine is collected and measured. When it is desired to empty urine from the receptacle 12, such as when it is full, the receptacle 12 is lifted from the container 14, and is placed in a tilted position such that the urine collects in an upper portion of the chamber 22 and passes from the chamber 22 through the conduit 48 into the container cavity 36 for retention therein. During this time, it is desirable to prevent the contact of urine against the bacteria filter in the vent 26, since such contacting urine may render the bacteria filter in the vent 26 inoperable. Also, it is desirable to prevent the reflux of urine from the receptacle chamber 22 into the drainage tube 16, since such refluxing urine may cause the passage of bacteria into the drainage tube 16 and by retrograde movement into the patient's bladder with possible deleterious results to the patient. Further, it is desirable to prevent the reflux of urine against the vent 26 and into the drainage tube 16 when the system 10 is mishandled, such as by turning the receptacle 12 into an inverted position. As will be seen below, the valve 18 in the receptacle 12 solves the problems associated with the prior liquid drainage systems.

With reference to FIGS. 1 and 2, the receptacle 12 has a baffle 50 extending across an upper portion of the chamber 22 below the vent 26 and drainage tube 16, and an annular wall 52 depending from the baffle 50.

The valve 18 comprises a cup-shaped member 54 of elastic material, such as rubber. The cup-shaped member 54 has a lower wall 56 extending across the cup-shaped member 54, and an upper annular wall 58 extending from the lower wall 56. As shown, an upper portion of the valve annular wall 58 is snugly and sealingly received on a lower portion of the receptacle annular wall 52 in order to retain the valve 18 in place. The valve 18 has a hinge member 60 extending outwardly from the cup-shaped member 54 at one side of the lower wall 56. The cup-shaped member 54 has a slit 62 extending through the cup-shaped member 54 to the hinge member 60 at a location slightly above the lower wall 56. In this form, the slit 62 defines an annular valve seat 64 above the lower wall 56, with the lower wall 56 serving as a valve element 66 which may sealingly engage against the seat 64, while the hinge member 60 connects the lower wall 56 or valve element 66 to the valve annular wall 58. As shown, the hinge member 60 has a vertical opening 68 spaced from the outer portions of the hinge member 60 and extending through the hinge member 60, with the slit 62 extending to the opening 68. In this manner, the opening 68 and slit 62 define a pair of spaced hinges 70 and 72 on opposed sides of the opening 68. In a preferred form, as shown, the cup-shaped member 54 has a greater thickness in the region of the lower wall 56 than in the upper portion of the valve annular wall 58.

With reference to FIG. 3, the hinge member 60 is divided into the hinges 70 and 72 in order to make the hinge member 60 weak and compliant enough to automatically open the valve element 66 from the seat 64 when the receptacle 12 is placed in an upright position. Thus, when the receptacle 12 is in an upright position, urine automatically flows through the valve 18 into a lower part of the chamber 22, with the vent 26 facilitating passage of the urine through the valve 18. However, with reference to FIG. 2, when urine refluxes against the valve element 66, such as when the receptacle 12 is tilted to pour urine from the chamber 22 through the conduit 48 into the cavity 36, the valve element 66 is closed against the seat 64 in sealing engagement to close the valve 18 and prevent passage of urine therethrough. When the receptacle 12 is tilted to pour urine from the chamber 22, the valve element 66 is suficiently flexible to vibrate and permit rapid passage of air from the vent 26 into a lower portion of the chamber 22 in order to replace the urine which passes from the chamber 22 during the emptying procedure. Also, when the receptacle 12 is mishandled, such as by placing it in an inverted position, the valve element 66 automatically closes against the seat 64 in order to prevent the reflux of urine through the valve 18. In this manner, the closed valve 18 prevents the reflux of urine against the vent 26 which might cause the bacteria filter in the vent 26 to become inoperable, and prevents the reflux of urine into the drainage tube 16 which otherwise might introduce bacteria into the drainage tube and by retrograde movement may pass into the patient's bladder with possible deleterious results to the patient. In accordance with the present invention, the hinge member 60 is divided into the two hinges 70 and 72 in order to guide the valve element 66 against the seat 64 in sealing engagement, such that the hinge member 60 resists swiveling which otherwise might result from a single hinge.

The foregoing detailed description is given for clearness of understanding only, and no unnecessary limitations should be understood therefrom, as modifications will be obvious to those skilled in the art.

I claim:

1. A liquid drainage system, comprising:
a receptacle having a chamber to receive liquid, and a depending annular wall in an upper portion of the receptacle; and
A valve comprising a cup-shaped member of elastic material having a lower wall extending across the cup-shaped member, an upper annular wall extending from said lower wall, with an upper portion of said valve annular wall being snugly received on a lower portion of the receptacle wall, and a hinge member extending outwardly from the cup-shaped member at one side of the lower wall, said cup-shaped member having a slit extending through the cup-shaped member to the hinge member at a location slightly above the lower wall, said slit defining a valve seat above the lower wall with the lower wall serving as a valve element which may sealingly engage against the seat, with said hinge member connecting the lower wall and valve annular wall, wherein said hinge member has a vertical opening spaced from an outer portion of the hinge member and extending therethrough, with said slit extending to the opening to define a pair of hinges on opposed sides of the opening.

2. The system of claim 1 including a vent communicating between the atmosphere and the valve at a location above the valve when the receptacle is in an upright position.

3. The system of claim 1 including a drainage tube communicating with the chamber at a location above the valve when the receptacle is located in an upright position.

4. The system of claim 1 including a container having a cavity.

5. The system of claim 4 including a conduit communicating between an upper portion of the chamber and an upper portion of the cavity.

6. The system of claim 1 wherein the receptacle wall extends from a baffle located in an upper portion of the chamber.

7. The system of claim 1 wherein said valve annular wall is thicker in the region of the lower wall than in the region of the upper portion of the valve annular wall.

* * * * *